United States Patent

Clegg et al.

[11] Patent Number: 5,938,905
[45] Date of Patent: Aug. 17, 1999

[54] HIGH-PRESSURE ELECTROPHORESIS APPARATUS AND METHOD

[75] Inventors: Robert Clegg; Leonardo Erijman, both of Gottingen, Germany

[73] Assignee: Max-Planck-Gesellschaft zur Forderung der Wissenschaften e.V., Munich, Germany

[21] Appl. No.: 08/808,430

[22] Filed: Feb. 28, 1997

[30] Foreign Application Priority Data

Feb. 28, 1996 [DE] Germany .......................... 196 07 546

[51] Int. Cl.⁶ .................................. G01N 27/26
[52] U.S. Cl. .......................... 204/455; 204/601; 204/605
[58] Field of Search .................... 204/451–455, 204/601–605

[56] References Cited

U.S. PATENT DOCUMENTS 5,292,420  3/1994  Nakanura ................................. 204/299
5,458,761  10/1995  Kamahori et al. ................... 204/299 R

OTHER PUBLICATIONS

Electrophoresis at elevated hydrostatic pressure of the multiheme hydroxylamine oxidoreductase, Masson et al, *Electrophoresis,* 1990, 11, pp. 128–133.

Hydrophobic interaction electrophoresis under high hydrostatic pressure: Study of the effects of pressure upon the interaction of serum albumin with a long–chain aliphatic ligand, Masson et al, *Electrophoresis,* 1988, 9, pp. 157–161.

Plurality of Protein Conformations of Ribulose–1,5–bisphosphate Carboxylase/Oxygenase Monomers Probed by High Pressure Electrophoresis, Erijman et al, The Journal of Biological Chemistry, vol. 268, No. 34, Issue of Dec. 5, 1993, pp. 25914–25919.

Analysis of Dissociation and Unfolding of Oligomeric Proteins Using a Flat Bed Gel Electrophoreseis at High Pressure, Paladini et al, *Analytical Biochemistry 218,* 1994, pp. 364–369.

Proteins under pressure, Gross et al., *Eur. J. Biochem.,* pp. 617–630, Feb. 1994.

Slab Gel Electrophoresis of Oligomeric Proteins under High Hydrostatic Pressure, Paladini et al, *Analytical Biochemistry,* 1987, pp. 358–364.

Pressure Stability of Proteins, Silva et al, *Annu. Rev. Phys. Chem.,* 1993, 44:89–113.

*Primary Examiner*—David A. Redding
*Attorney, Agent, or Firm*—Birch, Stewart, Kolasch & Birch, LLP

[57] ABSTRACT

A high-pressure electrophoresis apparatus is formed by a high-pressure tubing (101) in which at least one column-shaped cell is arranged, said cell comprising two cell portions being arranged in the operating condition one above the other which form a cathode buffer solution reservoir (12) and an anode buffer solution reservoir (123) separated by a supporting member (122) which supports a carrier column loadable with a separating gel. Following implementation of high-pressure electrophoresis the carrier gel is extruded from the carrier column and subjected to further electrophoresis at normal pressure implemented on a slab gel.

10 Claims, 4 Drawing Sheets

HIGH-PRESSURE ELECTROPHORESIS APPARATUS AND METHOD

FIELD OF THE INVENTION

The invention relates to an apparatus and a method for high-pressure electrophoretic sample separation.

DESCRIPTION OF THE RELATED ART

Exerting a high pressure is known to be an effective thermodynamic means of dissociating complex biological systems and of perturbing the conformation of macromolecules (see e.g. Silva, J. L. & Weber, G., Ann. Rev. Phys. Chem. 44, 89–113 (1993) and Gross, M. & Jaenicke, R., Eur. J. Biochem. 221, 617–630 (1994)). Electrophoresis, more particularly on the basis of carrier gels, has been demonstrated to be a suitable method of identifying the products dissociated at high-pressure. One example of a carrier gel electrophoresis is polyacrylamide gel electrophoresis (abbreviation: PAGE) with which preferably macromolecular components can be separated according to their size, charge and/or conformation. Implementing gel electrophoresis at high pressure is known, but until now has involved considerable experimental complications, however, or the following technical difficulties.

It is known to use in high-pressure gel electrophoresis so-called slab gels (see e.g. Paladini, A. A., Silva, J. L. & Weber, G., Anal. Biochem. 161, 358–369 (1987), Paladini, A. A., Weber, G. & Erijman, L., Anal. Biochem 218, 364–369 (1994) and Erijman, L., Paladini, A. A., Lorimer, G. H. & Weber, G., J. Biol. Chem. 268, 25914–25919 (1993) involving two-dimensional, flat gel arrangements preferably between glass plates. This technique is at a disadvantage because the slab gels necessitate relatively large high-pressure reservoirs. If high-pressure PAGE is to be implemented at specific temperature conditions this large high-pressure reservoir needs to be immersed in a complicated temperature control bath necessitating a lot of material and energy and precluding fast changes in temperature.

Furthermore, it is known e.g. from Masson, P. & Reyboud, J., Electrophoresis 9, 157–161 (1988) to implement PAGE with a tube filled with a carrier gel subjected to pressure. However, this technique is impractical because it is difficult to remove the tube gel, e.g. for staining, from the high-pressure tube in a nondestructive manner.

From the publication Masson, P., Arciero, D. M. Hopper, A. B. & Balny, C. Electrophoresis 11, 128–133 (1990) a high-pressure electrophoresis apparatus is known which is explained with reference to the schematic sectional illustration in FIG. 6. An outer glass centrifuge tube 607 having a diameter of 20 mm forms an anode buffer reservoir 601 in which the anode is fixed to a carrier 602. The cathode reservoir 604 is formed by a first inner tube 608, held by the carrier 602 within the anode reservoir 601 and by a second inner tube 609 applied by means of a passage disk 603 at the upper end of the first inner tube 608. A plurality of capillary tubes 605 loaded with the carrier gel is held by the carrier 602 and the passage disk 603 such that their ends protrude into the respective buffer solutions in the anode reservoir 601 and the cathode reservoir 604. The electrophoretic cell is closed off at its upper end by a pressure transmitting fluid 606 (silicone oil).

The electrophoretic cell known from FIG. 6 is, like the high-pressure electrophoresis apparatuses described above difficult to handle due to its complex configuration (arrangement of the buffer solution reservoirs in or alongside each other) and its bulkiness. The interengaging buffer reservoirs in which the charge transfer necessary for the electrophoresis takes place are configured voluminous to avoid excessive resistive heating. The electrophoresis apparatus according to FIG. 6 is restricted to laboratory apparatuses and is less suitable for carrying out routine investigations.

Due to the problems as cited and due to lack hitherto of measurement standards or means of calibration easy to handle high-pressure gel electrophoresis has been restricted hitherto to a few laboratory apparatuses.

Especially in biochemical and microbiological laboratories and also in corresponding production systems there is a major requirement for an analytical separation method which can be implemented time-savingly and evaluated quickly and reliably. These requirements fail to be satisfied by the high-pressure gel electrophoresis methods as described above.

SUMMARY OF THE INVENTION

It is thus the object of the invention to define an improved apparatus for implementing high-pressure electrophoresis with which the drawbacks of known apparatuses are overcome and which more particularly permit simple handling in routine operation, reliable evaluation and, where appropriate, uncomplicated further processing of the dissociated samples. It is furthermore the object of the invention to define an improved method of high-pressure electrophoresis and the evaluation thereof.

The above objects are achieved by a high-pressure electrophoresis apparatus including:
  a high-pressure vessel in which at least two buffer solution reservoirs are formed,
  at least one capillary carrier column loadable with a separating gel, each end of said column extending into one of said two buffer solution reservoirs respectively, and
  at least one column-shaped electrophoretic cell including two cell portions arranged one above the other in the operating condition which form said buffer solution reservoirs and which are separated by a supporting member supporting said carrier column.

The above objects are also achieved by an electrophoresis method using a separating gel in a capillary carrier column in an apparatus according to a high-pressure electrophoresis apparatus as described above, comprising the steps of:
  implementing a high-pressure electrophoresis in said capillary carrier column;
  extruding said separating gel from said carrier column; and
  implementing an electrophoresis at normal pressure in which said extruded separating gel is subjected to a separation on a slab gel arrangement.

In accordance with the invention at least one column-type electrophoretic cell is inserted in a high-pressure vessel, the cathode and anode buffer solution reservoirs of said electrophoretic cell being formed by two adjacent cell portions separated by a supporting member, a carrier column loadable with separation gel being mounted by the supporting member in such a way that its ends protrude into the buffer reservoirs. The supporting member forms preferably a substantially flat partition through which the carrier column passes. This configuration, which is much more simple and reducable in size as compared to conventional electrophoretic cells, is based on the idea of solving the problem of the heat dissipated in the buffer reservoirs not by increasing but by reducing the volume of the reservoirs. It having been surprisingly discovered that a reservoir geometry reduced in size and simplified, on the one hand, promotes uniform removal of heat to the environment and, on the other hand, permits the use of a relatively small and thus easily coolable high-pressure vessel. In keeping with a preferred embodiment of the high-pressure electrophoresis apparatus in accordance with the invention the latter is operated with highly concentrated buffer solutions to provide an adequate buffer capacity for the electrophoresis. The increase in concentration may advantageously amount to e.g. a factor 5 . . . 10 as compared to buffer concentrations in the case of conventional electrophoretic apparatuses.

The buffer solution reservoirs are arranged in accordance with the invention stacked to form a column. Whether the—in the operating condition—upper reservoir receives the cathode buffer solution or the anode buffer solution and the lower reservoir receives the solution of opposite buffer capacity in each case, depends on the specified conditions (e.g. molecule charging) in each case.

The method in accordance with the invention for implementing a high-pressure electrophoresis is based on the use of the high-pressure electrophoresis apparatus in accordance with the invention.

Contrary to the aforementioned problems in using tube gels the invention has surprisingly made it evident that the arrangement of the separation gel in a tubular form of reduced diameter permits, on the one hand, achieving a high separation resolution and, on the other hand, a simple nondestructive or non-damaging removal of the separation gel from the tubular form for further processing following high-pressure electrophoresis.

In accordance with the invention further gel processing following high-pressure electrophoresis may involve e.g. staining or repeat separation. In accordance with a preferred embodiment of this method in accordance with the invention the carrier gel following its removal from a carrier column is subjected to further slab gel electrophoresis carried out at normal pressure. This in result so-called two-dimensional electrophoresis permits a substantially sharper and more reliable separation of the components contained in a sample than is possible by conventional methods of high-pressure electrophoresis.

Details and advantages of the invention as well as the methodology in accordance with the invention will now be described in the following on the basis of an embodiment with respect to the appended figures.

BRIEF DESCRIPTION OF THE DRAWING

In this example the cathode is provided at the upper and the anode at the lower in the column arrangement. Although it will be appreciated that this electrode configuration is cited merely by way of example and may be inversed in a practical application (anode at the upper end, cathode at the lower end). In the drawing.

DESCRIPTION OF THE PREFERRED EMBODIMENTS

Figure 1:
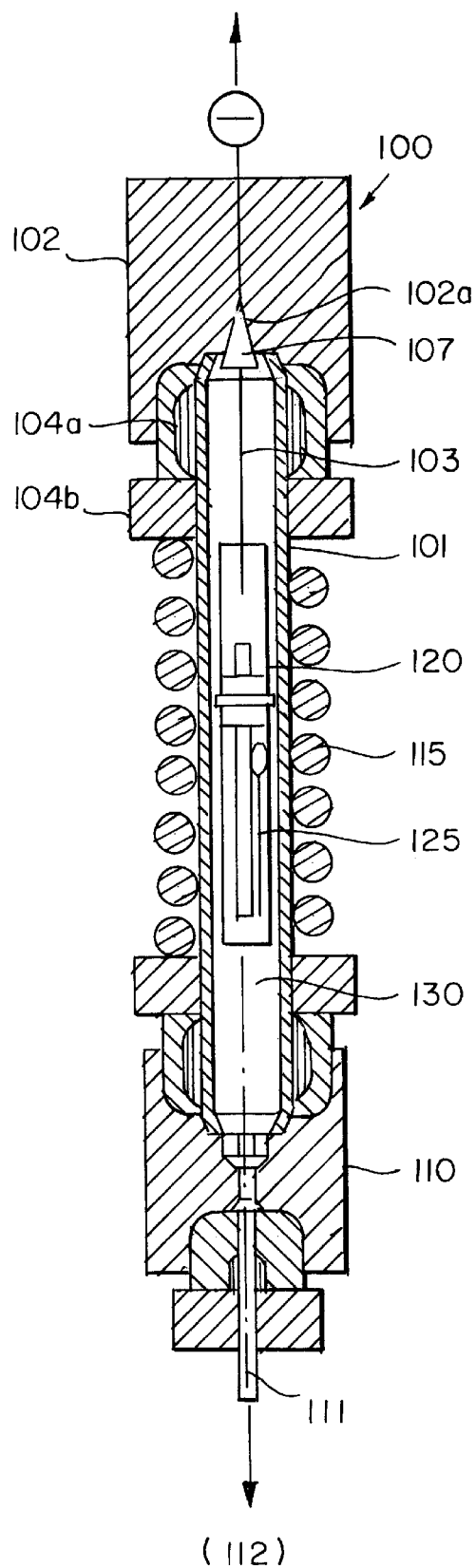
FIG. 1 is a schematic section view of a high-pressure electrophoresis apparatus in accordance with one embodiment of the invention.

FIG. 1 shows a schematic section view of the high-pressure electrophoresis apparatus 100 in accordance with the invention in the operating condition.

A high-pressure vessel is formed by metal high-pressure tubing 101 consisting of a high pressure resistant material, e.g. steel or a plastics material having an electrically conductive inner wall. The ends of the high-pressure tubing 101 are provided with high-pressure connectors 102, 110 with the use of high-pressure sleeves 104a and bush nuts 104b. The high-pressure connector 102 which is at the upper in the operating condition of the high-pressure electrophoresis apparatus is provided for pressure-tight passage of the cathode 103 and its connection to a power supply (not shown). The cathode 103 will be described below in more detail with reference to FIG. 3. The opposite, lower high-pressure connector 110 contains a pressure conduit 111 leading to a high-pressure generator 112 (not shown).

For the high-pressure tubing 101 any commercially available high-pressure tubing may be employed. The dimensions of the high-pressure tubing illustrated in FIG. 1 are e.g. 8 mm (inner diameter) and 14.3 mm (outer diameter).

The high-pressure generator 112 may be formed e.g. by a worm-type displacement generator. The high-pressure tubing 101 is fillable with an electrically conductive pressure fluid 130 (e.g. silicone oil, viscosity: 200 cS) If the pump is operated with a fluid other than silicone oil it is possible to provide between the pump and the high-pressure tubing a separating means, as is known e.g., from Spitzer, M. et al., Rev. Sci. Instrum. 59, 2092–2093 (1988). Instead of this, however, a rubber plunger may be provided in the pressure conduit leading from the pump 112 to the high-pressure tubing 101 to separate both pressure fluids from each other without any appreciable contamination.

Figure 2:
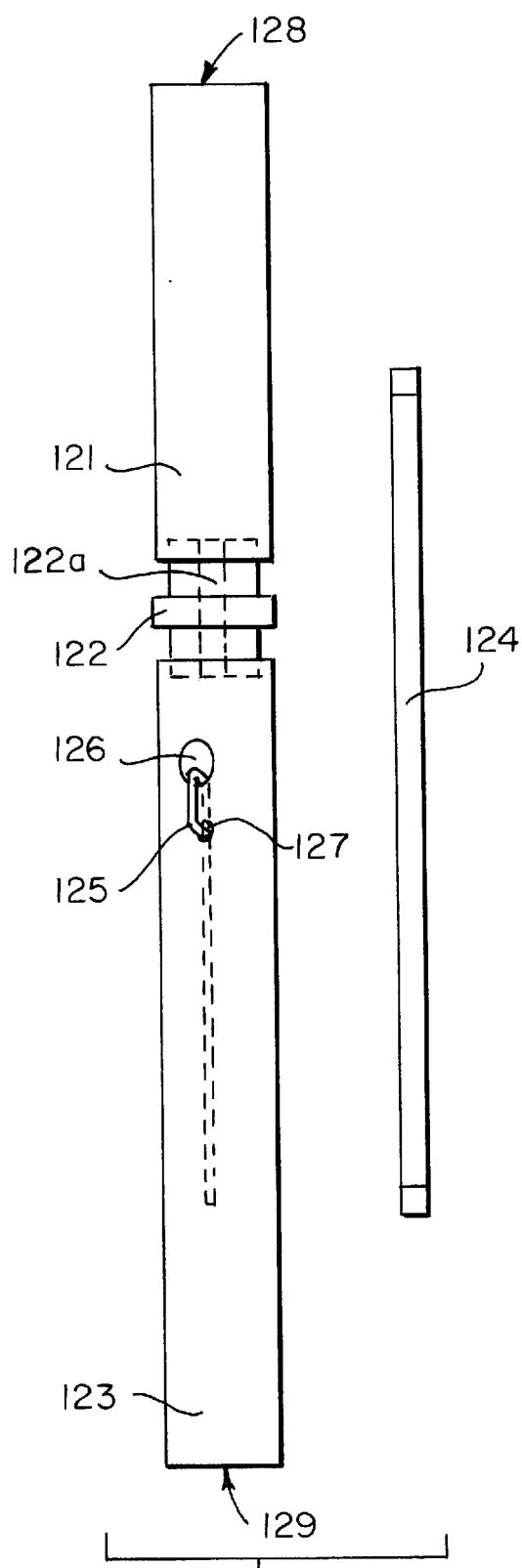
FIG. 2 is a schematic magnified view from above of the electrophoretic cell shown in FIG. 1.

In the interior of the high-pressure tubing 101 a removable column-type electrophoretic cell 120 is arranged which will now be detained with respect to FIG. 2. In the operating condition the electrophoretic cell 120 is positioned in the high-pressure tubing 101 by the clamping effect of the anode 125 such that the cathode 103 introduced into the upper end of the high-pressure tubing 101 protrudes into the upper cell portion of the electrophoretic cell 120 which forms a cathode buffer reservoir.

The high-pressure tubing 101 is surrounded from without by a temperature control means. The latter may be formed e.g. by a cooling spiral 115 connected to a thermostat bath or any other suitable cooling element. Dimensioning the cathode 103 and positioning the electrophoretic cell 120 are preferably selected so that the electrophoretic cell 120 in the operating condition is located in the interior of the high-pressure tubing 101 substantially in the region of the outer cooling element.

The geometry and size of the electrophoretic cell 120, illustrated magnified in FIG. 2, are advantageously adapted to the dimensions and shape of the high-pressure tubing 101. In the case of the example embodiment the electrophoretic cell has an outer diameter of approximately 5 to 7 mm and a length of approximately 80 to 90 mm. The electrophoretic cell 120 is configured by three components separable from each other including the cathode buffer reservoir, the supporting or connector member 122 and the anode buffer reservoir 123. These components consist of an electrically non-conductive material, preferably a plastics material such as e.g. polychlorotrifluorethylene (trade name: Kel-F) or of glass. The column-type cathode buffer reservoir 121 has the form of a cylinder which at its—in the operating condition—upper end open is provided with an opening 128 and is attached to the supporting member 122 by its lower open end.

The supporting member 122 consists of a cylindrical component having the form of a double-sided connection stopper. The supporting member comprises an axial recess 122a, the diameter of which is adapted to the outer diameter of the carrier column 124 such that the latter can be received positively and buffer solution tight in the supporting member 122.

The anode buffer reservoir 123 arranged in the lower position in the operating condition is formed by a cylinder which is closed off at its lower end 129 and is applied by its open upper end to the supporting member 122. The wall of the reservoir 123 comprises furthermore an opening 126 for configuring the hydrostatic pressure in the interior of the anode reservoir 123 and, where appropriate, a further opening 127 for passage of the anode 125. The openings 126, 127 are dimensioned and arranged at such a level that during implementation of the electrophoresis no perturbing contamination of the interior space of the anode reservoir can occur.

The anode 125 consists of a platinum wire oriented parallel to the inner wall of the anode reservoir 123 and is secured at its upper end to the openings 126, 127, bent to form a loop. The anode 125 thus has a dual function. Firstly, it produces the contact to the wall of the high-pressure tubing 101, the latter being connected to the anode of the power supply (not shown). Secondly, the wire loop conduit in the operating condition a simple means of mounting the electrophoretic cell 120 in the interior of the high-pressure tubing 101, by the electrophoretic cell 120 being clamped against the inner wall of the high-pressure tubing 101 (spring effect). For reasons of a clear view FIG. 1 merely shows the contact of the anode 125 to the inner side of the high-pressure tubing 101, but not the inclined mounting position of the electrophoretic cell 120, where appropriate, and the contact to the opposing tubing wall.

The carrier column 124, loadable with a separating gel as illustrated in FIG. 2 along with the electrophoretic cell 120 are received in the operating condition of the high-pressure electrophoresis apparatus by the supporting member 122 in such a way that its ends protrude into the anode or cathode buffer reservoirs 121, 123.

The stopper-type connector of the buffer reservoirs 121, 123 with the supporting member 122 permits facilitated replacement with the supporting members, the axial passage of which has a modified inner diameter so that the electrophoretic cell 120 can be adapted simply to carrier columns 124 of differing diameters.

Figure 3:
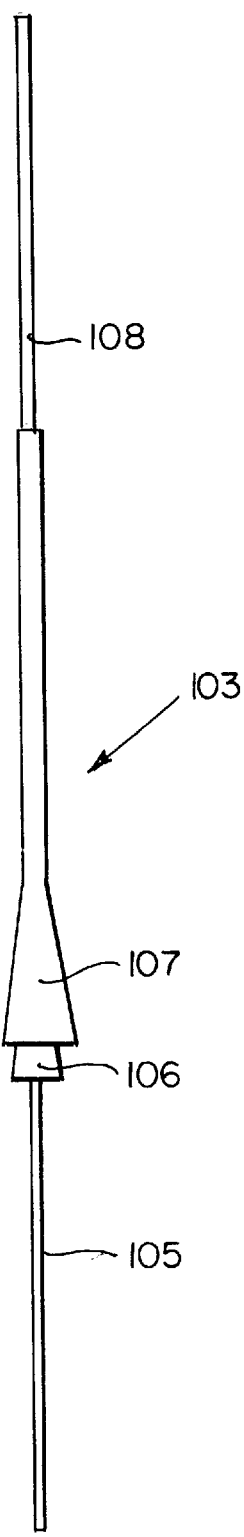
FIG. 3 is a schematic magnified view from above of the cathode leadthrough of the apparatus shown in FIG. 1.
Figure 6:
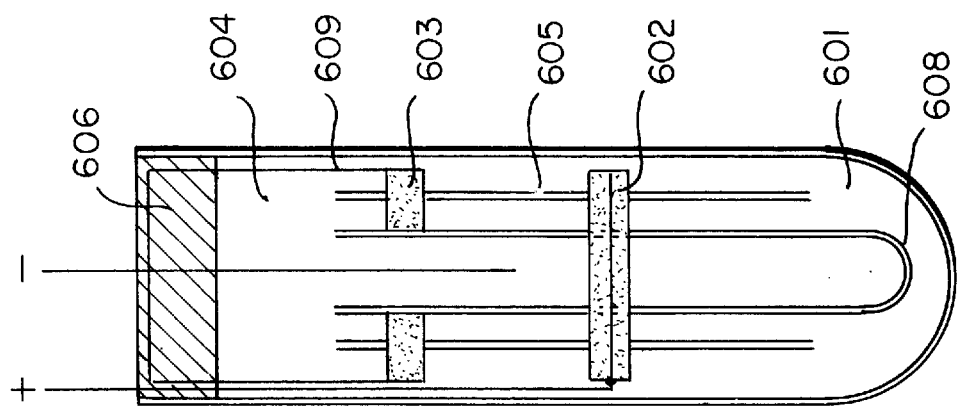
FIG. 6 is a schematic section view of a conventional high-pressure electrophoretic cell.

Details of the upper electrode (cathode) shown in FIG. 1 are illustrated in FIG. 3. The cathode 103 consists of a platinum wire 105 soldered to the base side of a steel cone 106. Soldered to the tip of the steel cone 106 is a steel rod 108 providing the connection to the cathode of the power supply. The steel cone 106 and the steel rod 108 are provided with an electrical insulation which is formed by a partly conically configured sleeve 107 of PTFE (Teflon, reg. mark). The steel cone 106 may feature, for example, a conical angle of 9°. The PTFE insulation may, for example, have a thickness of 0.25 to 1 mm.

The high-pressure connector 102 shown in FIG. 1 comprises an axial drilled bore which translates at the side facing the high-pressure tubing 101 into a conically flared portion 102a forming with the conical portion of the PTFE insulation 107 an effective pressure seal of the electrical connection from the power supply in the high-pressure reservoir by simple means.

The operation of the high-pressure electrophoresis apparatus in accordance with the invention will now be described with reference to FIGS. 1 to 3. To begin with, a capillary-type carrier column having a suitable inner diameter of approximately 0.5 mm to 2 mm is loaded with the separating gel in accordance with a known method. For the carrier column any commercially available capillary pipette (e.g. 5–50 ml pipette) may be used after it having been cut to length. The carrier column was cut to a column roughly 45 mm in length. Acrylamide solutions were polymerized in batches of 5 ml, the solutions degassed and filled into the carrier column by capillary action so that roughly 4 mm remained vacant at the one end of the column for receiving the sample. Gelling then followed under the effect of water-saturated isopropanol and resolved roughly 1 hour prior to use of the carrier column. Using discontinuous gel systems consisting of a loading gel and a separating gel is possible.

The composition of the cathode buffer in the cathode buffer reservoir 121 is formed by Tris-(24 mM)-glycine (192 mM) with a pH=8.2. As compared to this, the Tris-glycine buffer in the anode buffer reservoir 123 is approximately 5 times more concentrated. As in conventional electrophoresis apparatuses the buffer conditions and the nature of the buffer can be varied.

The samples were loaded, for example, with a 0.2–2 ml micropipette into the upper gel-free receiving space of the carrier column 124. The electrophoretic cell 120 with the loaded carrier column 124 and the buffer solutions was then immersed in the high-pressure tubing 101 filled with silicone oil, whereby an actuating means (manipulator, pinzette or the like, not shown) was used. After being closed off, the interior of the high-pressure tubing 101 was exposed to a predetermined pressure and a predetermined temperature. After roughly 15 to 20 minutes for equilibration the electrodes for implementing electrophoretic separation were connected to a voltage of roughly 100 V for approximately 60 minutes.

On completion of separation the carrier column 124 was removed from the high-pressure tubing 101 or electrophoretic cell 120 and the gel extruded from the carrier column 124. This is done preferably by exerting a water pressure e.g. by a syringe which is connected via plastics tubing to the carrier column, or mechanically with a thin plunger suitable for introducing into the capillary. Further processing involved introducing the gel into a staining solution or, where appropriate, implementing a second step in the electrophoresis at normal pressure.

For this subsequent PAGE, which was carried out preferably discontinuously, the extruded gel in a stacking gel buffer was brought into contact with a warm solution of 1% agarose. Starting with this stacking gel buffer the second step in electrophoresis was implemented using a slab gel which, where applicable, was loaded for calibration purposes at the same time with separate control solutions.

This so-called two-dimensional separation permits a more precise interpretation of the bands obtained in capillary gel electrophoresis which may be relatively blurred in some circumstances. This blurring is not due the apparatus or the method, it instead being a thermodynamic result of the distribution of the free enthalpy in the system of the components to be separated. This made it possible for the first time to identify sub-units of aggregated systems which hitherto were unseparable.

Preferably, the second separation is implemented with a sodium sulfate slab gel (so-called SDS-PAGE) to further resolve the bands having resulted in the high-pressure gel.

Two-dimensional separation may also be implemented with high-pressure gels from conventional column arrangements. Electrophoresis separation of two example samples will now be described with reference to FIGS. 4, 5A and 5B.

(a) Sample 1

Figure 4:
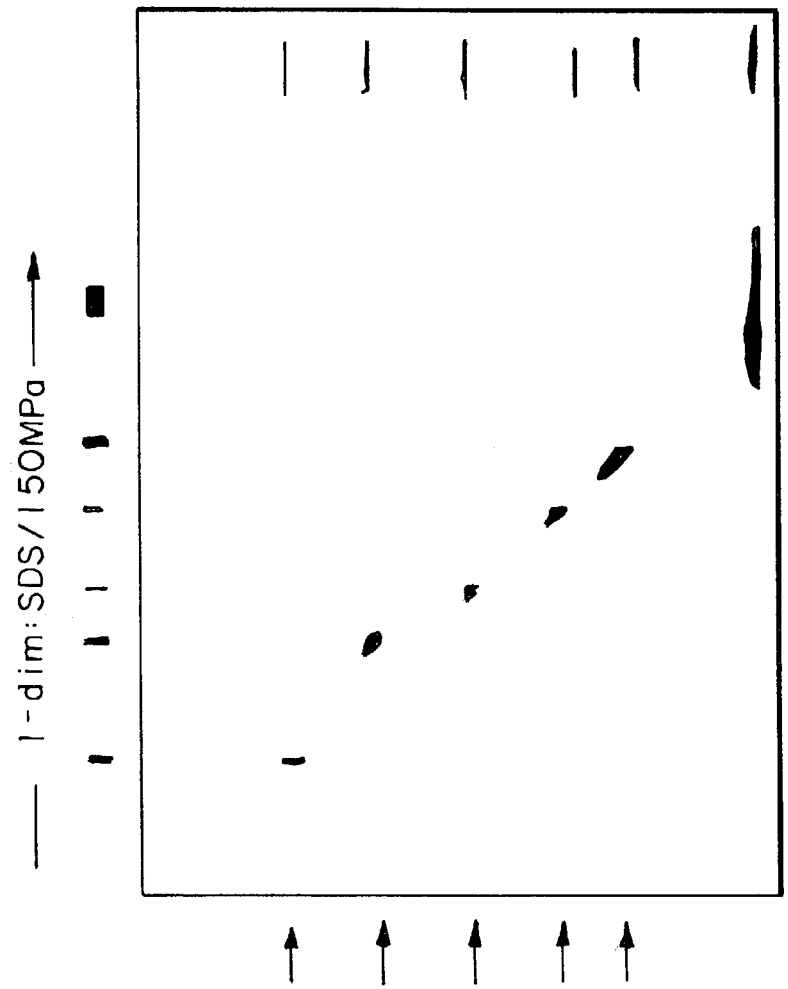
FIG. 4 shows the result of a single and two-dimensional PAGE of molecular weight markers.

FIG. 4 shows the result of one and two-dimensional PAGE separations of pre-stained molecular weight markers. The upper portion of this figure shows the result of the first separation by means of the high-pressure electrophoresis apparatus as described above (method parameters: inner diameter of carrier column: 1 mm, pressure 150 MPa, voltage 100 V, duration 60 minutes).

The bands formed as a result of the second separation with the slab gel on the separation surface area are sharply distinguished and show no spreading or profiling. This result shows that high-pressure electrophoresis advantageously features basically the same resolution as subsequent slab gel electrophoresis at normal pressure. The result further shows that electrophoresis at 150 MPa results in no deformation or other negative effect of the gel.

(b) Sample 2

Figure 5A:
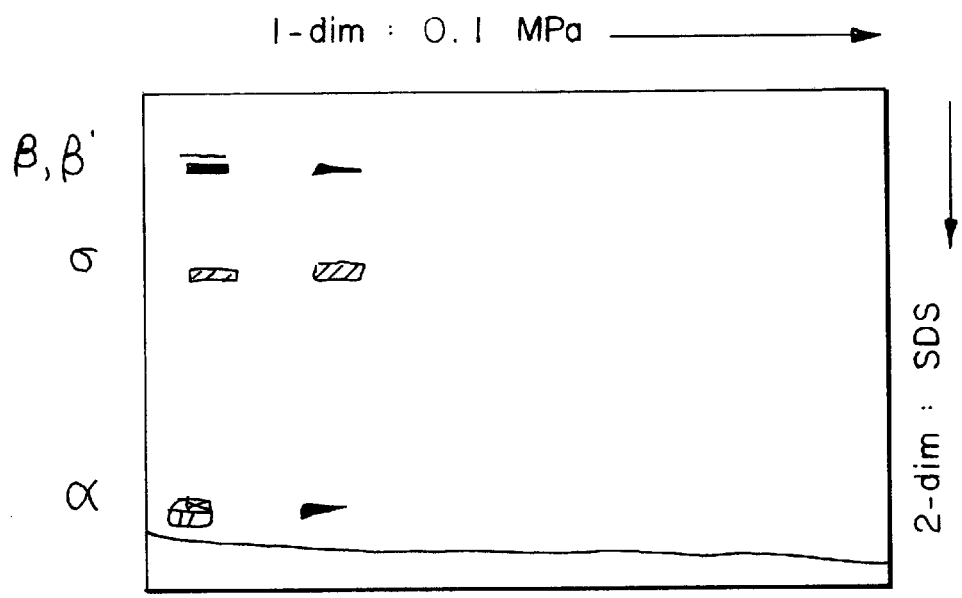
FIGS. 5A and 5B show the results of two-dimensional separations of sub-units of *E.coli* RNA polymerase.
Figure 5B:
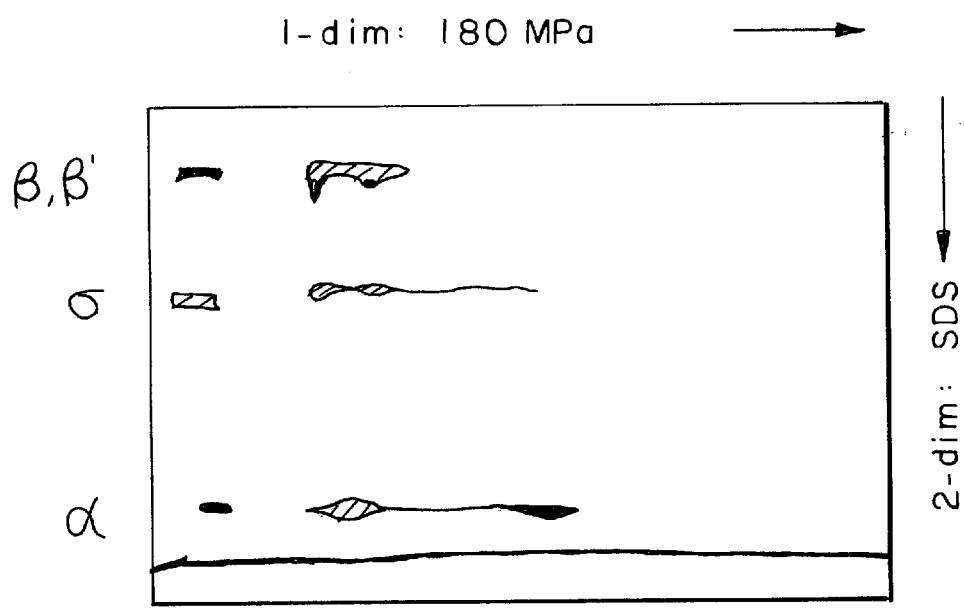

The separation of the enzyme E. coli RNA polymerase (RNAP in the following) consisting of a plurality of sub-units is shown in FIG. 5A and FIG. 5B respectively for normal pressure and at pressures above 120 MPa. Due to technical limitations in printing, these figures show the location of the bands merely schematically and without gray steps. Relatively weak bands are shaded. To obtain more detailed information as to conformation and integrity of the polygomer complex when subjected to high pressure the gels obtained in the narrow-bore, capillary carrier column were separated in a second dimension using a slab gel. For this purpose the gel was loaded from the carrier column onto a standard mini-slab gel in the presence of sodium dodecyl sulfate (so-called SDS PAGE). The second separation with subsequent staining permits identifying the sub-units by comparing their mobility to that of a standard sample which has not been produced under pressure and loaded on the same gel. Comparing the bands in the sodium dodecyl sulfate slab gel (from the extruded high-pressure gel) to a control experiment, in which the first dimension was obtained at normal pressure shows the dissociation of the RNAP holoenzyme in its sub-units at 180 MPa. As expected the control experiment shows no dissociation of RNAP at normal pressure (FIG. 5A), whereas at elevated pressure the protein materials after separation from the various bands from the high-pressure gel show various mobilities in the slab gel in keeping with the individual sub-units of the RNAP (s FIG. 5B). This shows that the sub-units are separated in high-pressure electrophoresis without denaturants and move according to their size and charge, whereby β' identifies the basic sub-unit of RNAP (see Zillig, W et al., RNA Polymerase, Cold Spring Harbor Laboratory, 1976).

The visibly broad bands in FIG. 5B are attributed to the statistically distributed free energy of unification of the sub-units at the pressure at which the gel is used. If the protein sub-units enter into interaction differentially at elevated pressures, no well-defined spots (as in FIG. 4) but spreaded bands are anticipated, the size of which depends on the degree of dissociation or the pressure applied.

The apparatus and method in accordance with the present invention feature the following advantages.

The simple handling of the high-pressure electrophoresis apparatus permits implementing at little expense a plurality of sample separations by varying the parameters pressure, temperature, pH, gel concentration etc.

The measurements are achievable at the slight expense of modifying available low-cost and commercially available instruments. Considerable cost and space saving aspects are achieved in enabling routine implementation of sample separations. Since any standard high-pressure connector may be used as the high-pressure tube which as a rule is offered by the manufacturer safety-tested (in Germany e.g. by the Technical Inspectorate Authority) high operational reliability is achieved at low cost.

The apparatus in accordance with the invention enables large amounts of heat to be effectively removed by immersing the complete small-diameter electrophoretic cell in the surrounding silicone oil which has a high heating capacity. Simultaneously it is possible to adjust specific temperatures for specific conditions of dissociation and to quickly vary the temperatures. The column shape of the electrophoretic cell and high-pressure tube permits furthermore the amount of high-pressure fluid required as a whole to be reduced, thus making relatively small high-pressure pumps applicable.

Since the high-pressure gels can be easily extruded from the carrier column two-dimensional separation is possible in accordance with the invention. The arrangement of the extruded gel along one edge of an electrophoresis sodium dodecyl sulfate slab gel enables the sub-units separated at elevated pressure to be identified and further analyzed in the second electrophoresis implemented at normal pressure, thus achieving a considerable gain in information as to implementing quantitative thermodynamic analyses of complex enzymes by the so-called RNAP system. It is furthermore possible to cut out a section of the high-pressure gel and subject it to further high-pressure electrophoresis so that the formation of further sub-bands can be investigated.

The apparatus and method in accordance with the invention are applicable in the following fields: investigating the arrangement of enzymes having several sub-units, heterogenic molecular aggregates, membranes and membrane complexes, viruses and cells. It is possible to separate protein complexes comprising several sub-units into their components without solvent or denaturants and to recombine them following treatment of the individual sub-units (e.g. applying fluorescent markers). Due to the freezing point of water being lowered at high pressure an electrophoresis analysis of the protein development at temperatures below zero (so-called cold denaturing) is made possible. Furthermore, it is feasible to separate epitopes (e.g. using whole viruses) in avoiding the use of organic solvents.

Due to the compactness of the electrophoretic cell a plurality of high-pressure electrophoresis runs may be implemented at the same time using several cells in a high-pressure reservoir or in several high-pressure reservoirs. If only one pressure generator is available, even a plurality of measurements can be carried out at various pressures by making use of high-pressure valves in various high-pressure reservoirs. When making use of suitable high-pressure components the apparatus may also find application at pressures higher than the 200 MPa tested in this case.

By employing high-pressure tubes differing in length the length of the carrier column may also be simply modified thus enabling a high-pressure electrophoresis apparatus to be configured to any length without any considerable increase in expense or cost.

What is claimed is:

1. A high-pressure electophoresis apparatus comprising:

a high-pressure vessel in which at least two buffer solution reservoirs are formed, at least one capillary carrier column loadable with a separating gel, each end of said column extending into one of said two buffer solution reservoirs, respectively, and at least one column-shaped electrophoretic cell including two cell portions arranged one above the other in the operating condition which form said buffer solution reservoirs and which are separated by a supporting member supporting said carrier column.

2. The apparatus as set forth in claim 1, wherein a first reservoir of said buffer solution reservoirs, as the upper reservoir in the operating condition, is formed by a plastic cylinder, the upper end of which is attached to said supporting member and the upper end of which is open.

3. The apparatus as set forth in claim 2, wherein a second reservoir of solution reservoirs, as the lower reservoir in the operating condition, is formed by a plastic cylinder, the upper end of which is attached to said supporting member and the lower end of which is closed off.

4. The apparatus as set forth in claim 1, wherein said supporting member has the form of a double-sided stopper with an axial recess for receiving said carrier column and is inserted in the lower or upper end of said buffer solution reservoirs.

5. The apparatus as set forth in claim 1, wherein said high-pressure vessel is formed by metallic high-pressure tubing.

6. The apparatus as set forth in claim 5, wherein one electrode extends, in operating condition, from an upper insulated leadthrough in a high-pressure connector of said high-pressure tubing into said upper buffer solution reservoir.

7. The apparatus as set forth in claim 5 or 6, wherein a counter-electrode is formed by a metallic element located in the interior of said lower buffer solution reservoir, said element forming a springy loop protruding through at least one opening from said lower buffer solution reservoir such that in the operating condition an electrical contact is formed with the inner wall of said high-pressure tubing.

8. The apparatus as set forth in claim 7, wherein said counter-electrode protrudes from said lower buffer solution reservoir so far that in the operating condition said electrophoretic cell is clamped in said high-pressure tubing against the inner wall thereof.

9. The apparatus as set forth in claim 7 wherein said electrode is a cathode or an anode and said counter-electrode is of a corresponding opposite polarity.

10. An electrophoresis method using a separating gel in a capillary carrier column in a apparatus according to claim 1, comprising the steps of:

implementing a high-pressure electrophoresis in said capillary carrier column;

extruding said separating gel from said carrier column; and implementing an electrophoresis at normal pressure in which said extruded separating gel is subjected to a separation on a slab gel arrangement.

* * * * *